United States Patent [19]

Deniega et al.

[11] Patent Number: 4,964,559

[45] Date of Patent: Oct. 23, 1990

[54] PNEUMATIC SURGICAL STAPLER CONNECTORS

[75] Inventors: Jess Deniega; Bela Vincze, both of Flemington; Jack Pedlick, Butler, all of N.J.

[73] Assignee: Ethicon, Inc., Somerville, N.J.

[21] Appl. No.: 294,540

[22] Filed: Jan. 9, 1989

[30] Foreign Application Priority Data

Jan. 15, 1988 [GB] United Kingdom ............... 8800909

[51] Int. Cl.⁵ .................................... A61B 17/00
[52] U.S. Cl. .................................. 227/178; 227/19; 285/136
[58] Field of Search ................ 227/19, 176–177, 227/178, 179, 180, 181, 182; 285/136

[56] References Cited

U.S. PATENT DOCUMENTS

| | | |
|---|---|---|
| 2,662,785 | 12/1953 | Fawick ............................ 285/136 |
| 3,004,588 | 10/1961 | Christenson .................. 285/136 X |
| 3,527,482 | 9/1970 | Casterline et al. ............... 285/136 |
| 3,613,507 | 10/1971 | Smith . |
| 3,618,842 | 11/1971 | Bryan . |
| 3,643,851 | 2/1972 | Green et al. . |
| 3,662,939 | 5/1972 | Bryan . |
| 3,717,294 | 2/1973 | Green . |
| 3,815,476 | 6/1974 | Green et al. . |
| 3,836,116 | 9/1974 | Noiles . |
| 3,837,555 | 9/1974 | Green . |
| 4,142,742 | 3/1979 | Cornett et al. .................. 285/136 |
| 4,260,382 | 4/1981 | Thomson ...................... 285/136 X |
| 4,331,277 | 5/1982 | Green . |
| 4,349,028 | 9/1982 | Green . |
| 4,407,432 | 10/1983 | Shichman . |
| 4,869,414 | 9/1989 | Green et al. ...................... 227/19 |

FOREIGN PATENT DOCUMENTS

| | | | |
|---|---|---|---|
| 332296 | 11/1935 | Italy ................................ 285/136 |
| 27491 | 11/1910 | United Kingdom ............. 285/136 |
| 2000568 | 1/1979 | United Kingdom ............. 285/136 |

*Primary Examiner*—Paul A. Bell
*Attorney, Agent, or Firm*—Paul A. Colletti

[57] ABSTRACT

A pneumatic connector for a surgical stapler is provided to enable interconnected parts of the stapler to be rotatable with respect to each other while maintaining the fluidic integrity of a plurality of pneumatic lines passing through the connector. One pneumatic line is connected to pass through the center of the pneumatic connector. The second pneumatic line is annularly rotatable around the first. The second line is rotatably completed and sealed by means of an annular mating passageway.

15 Claims, 3 Drawing Sheets

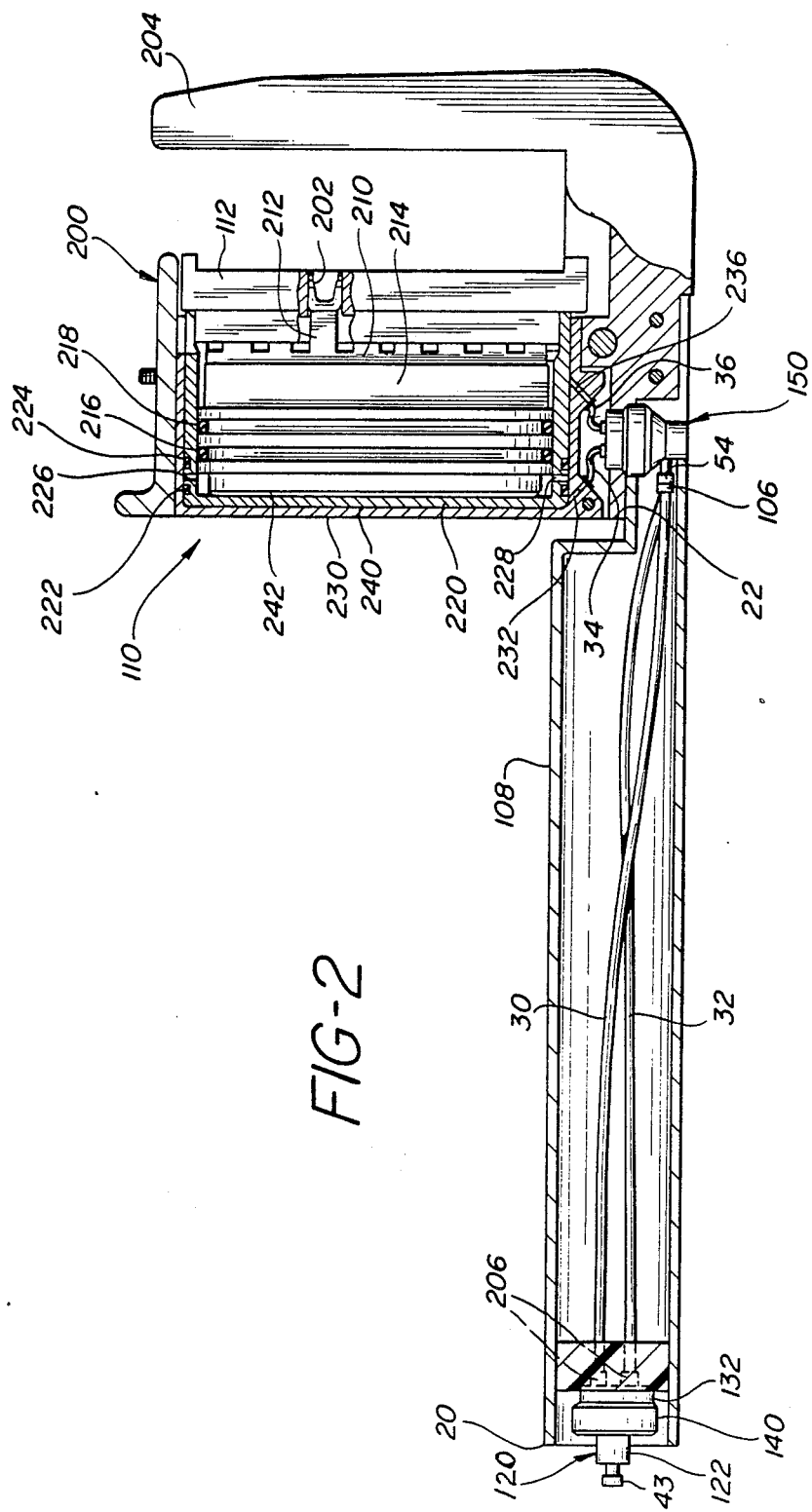

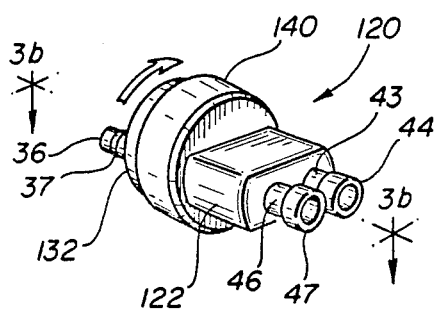
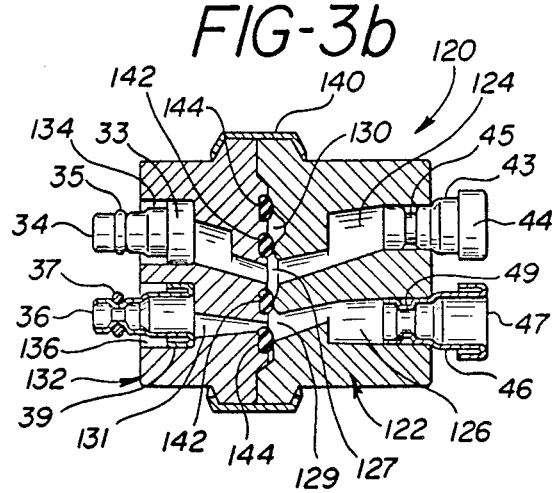
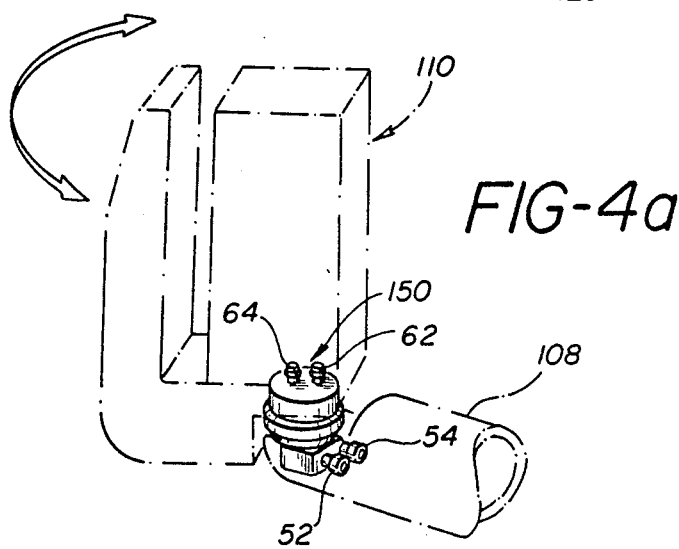
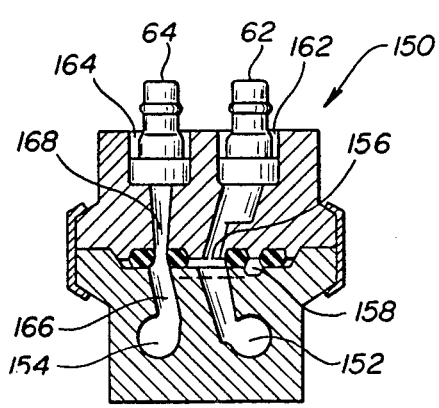
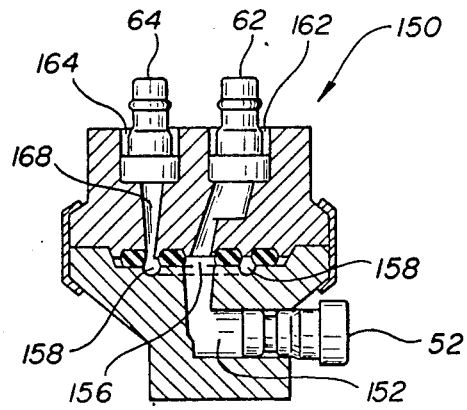

PNEUMATIC SURGICAL STAPLER CONNECTORS

This invention relates to surgical staplers for implanting mechanical surgical fasteners in the tissue of a patient, and, in particular, to surgical staplers which are powered by pressurized gas.

Surgical staplers which implant surgical fasteners using the force of pressurized gas are known in the art, and are described in U.S. Pat. Nos. 3,837,555; 3,836,116; 3,815,476; 3,717,294; 3,662,939; 3,643,851; 3,618,842; 3,613,507; 4,407,432; 4,439,028; and 4,331,277, among others. In the instruments shown in these patents, a cylinder of pressurized gas is contained in the handle of the instrument. Gas from the cylinder is conducted to a power unit at the rear of the handle, where the pressurized gas is applied to the proximal end of a mechanical linkage arrangement. The mechanical linkage is connected to a staple cartridge at the distal end of the instrument. When the trigger on the handle is depressed, pressurized gas actuates the mechanical linkage to implant a staple from the distally located cartridge.

All of the instruments shown in the above patents deliver a single staple upon each actuation of the instrument. It would be desirable for a pneumatic stapler to implant several staples at each actuation of the instrument, such as is performed by the linear stapler shown in U.S. Pat. No. 4,527,724. The instrument of this invention is capable of implanting two rows of staples upon each actuation of the instrument.

The surgical stapling instruments of the above patents are all rigidly constructed, constraining the use of the instrument to a single configuration. It would be desirable for the user to be able to rotate and pivot the various sections of the stapling instrument relative to each other, such as is shown in U.S. Pat. No. 4,728,020. In the instrument shown in this patent, the fastener applying assembly, or stapler head, is capable of swinging approximately 180° to either side of the axis of the shaft assembly of the instrument, and the stapler head is also capable of rotation through an arc of approximately 300° about the axis of the shaft. Such rotation allows the instrument to be manipulated for better ease of surgical use and to access difficult surgical sites.

When adapting a pneumatically energized linear stapling instrument for such pivoting and rotation, consideration must be given to the manner in which the force of the pressurized gas is delivered to the stapler head. It is preferable to deliver the pressurized gas directly to the stapler head to eliminate the numerous parts and complexity of any intermediate mechanical linkage. This complicates the rotating and pivoting joints of the instrument, which then must be capable of the desired movement while maintaining the integrity of the gas delivery system. In particular, it is desirable to deliver two separate sources of pressurized gas to the stapler head: one to clamp the stapler head against the tissue being stapled, and a second to actuate the means for driving the staples through the tissue. Thus it is desirable for the movable joints in the instrument to exhibit the desired range of movement and to do so in a manner which preserves the integrity of the two gas delivery lines.

In accordance with the principles of the present invention, a pneumatically actuated stapling instrument is provided which includes at least one connector capable of rotation about a given axis. The rotatable connector includes a first coaxial passageway extending through the connector for delivery of pressurized gas to one utilization means in the stapler head. The connector also includes a second passageway which radially surrounds said first passageway for delivery of pressurized gas to a second utilization means in the stapler head. Use of the connector of the present invention permits two connected portions of the instrument to be moved relative to each other while preserving the integrity of the two gas lines passing through the connector. The connector is especially useful in an articulated pneumatic surgical stapling instrument requiring a first source of pressurized gas to clamp tissue in the stapler head and a second source of pressurized gas to staple the clamped tissue.

In the drawings:

FIG. 2 shows the shaft and stapler head of a surgical stapler utilizing the connectors of the present invention; and FIGS. 3a, 3b and 4a–4c show rotating connectors of the present invention with quick disconnect fittings for connecting various modular components of a surgical stapler.

Figure 1:
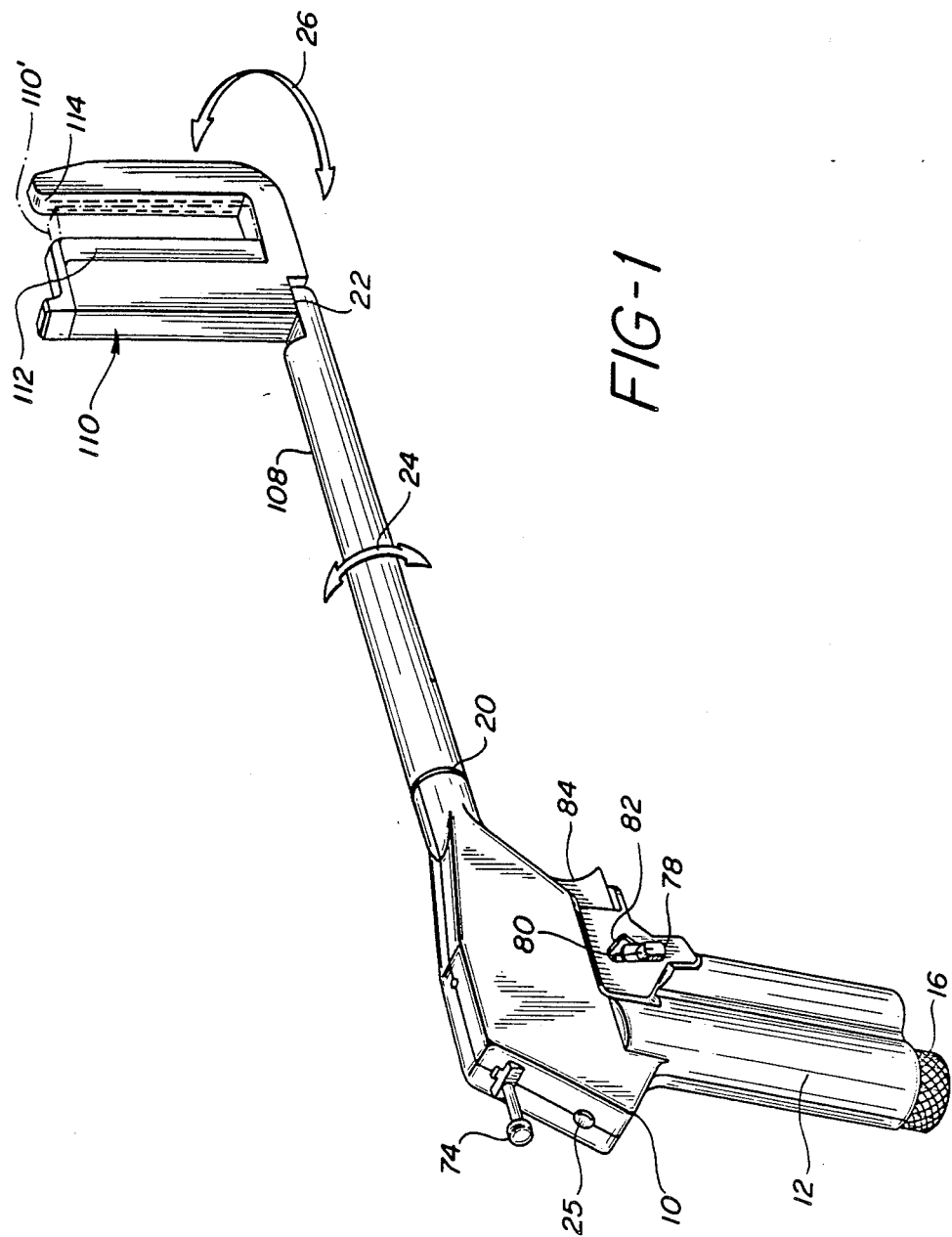
FIG. 1 is a perspective view of a surgical stapler utilizing the connectors of the present invention.

Referring first to FIG. 1, a pneumatically actuated surgical stapler of the present invention is shown. The stapler includes three major components: a handle portion 10, a shaft portion 108, and a stapler head 110. The three components are joined at their interconnecting points by pneumatic quick-disconnect fittings which allow the components to be disconnected and interchanged with shafts and stapler heads of other configurations. Also located at the joints 20 and 22 are pneumatic rotatable connectors of the present invention. The rotatable connectors allow free rotation of the major components of the stapler with respect to each other, as indicated by the arrows 24 and 26. Specifically, the shaft 108 is free to rotate completely about its axis at the joint 20 as indicated by arrow 24. The stapler head 110 is free to rotate greater than 200° about an axis which is normal to the axis of the shaft 108, as indicated by arrow 26.

A cylinder of pressurized gas is inserted into the lower portion 12 of the handle 10 by removing the cap 16 and inserting the cylinder into the handle. Once the cylinder has been inserted and the cap 16 tightened, gas from the cylinder is released and flows to a pressure regulator in the handle. The release of gas from the cylinder arms the stapler and causes a button 25 to extend a short distance out the rear of the handle, indicating to the user that the stapler is pressurized.

The first step in a stapling procedure is to clamp the tissue to be stapled between the jaws of the stapler head 110. The tissue is located between the jaws, and a slide 74 which extends from the rear of the stapler is depressed. When the slide is pressed forward, pressurized gas is allowed to flow to the stapler head through a first gas line to clamp the tissue between the jaws of the stapler head. As soon as the slide 74 is released, it slides back to its illustrated extended position by spring force. The position of the rearward portion of the stapler head after clamping is shown in phantom at 110' in FIG. 1.

Staples in a cartridge 112 may then be driven through the clamped tissue by depressing the trigger 84 of the handle. Before the trigger can be depressed, however, a trigger safety 78 must be moved upward in its slot 80 from the position shown in FIG. 1 and rotated into a forward extension 82 of the slot 80. This safety mechanism prevents inadvertent placement of the staples before the user is ready to do so. After the trigger safety 78 has been moved up and rotated forward the trigger may be depressed to implant the staples in the tissue, either by clinching the legs of the staples against an anvil 114 in the stapler head 110 or by interlocking the legs of the staples with connecting staple receivers located in the position of the anvil. As the trigger 84 is depressed, the trigger safety is rotated back to its more vertical position and slides downward in slot 80 by spring force.

FIG. 2 is a partial cross-sectional illustration of shaft 108 and stapler head 110. The stapler head includes a jaw 200 which carries a plurality of staples 202 in a movable clamping and stapling mechanism. Opposite the jaw 200 is a stationary opposing jaw 204. The face of the stationary jaw which opposes the stapling mechanism comprises an anvil which clinches or bends the legs of metal staples which pass through the tissue between the jaws. Alternatively, when the staples are formed of absorbable polymeric materials, the stationary jaw carries a cartridge of receivers which mate with and retain the legs of the polymeric staples. Such polymeric staples and receivers are described in U.S. Pat. No. application Ser. No. 117,592, filed Nov. 5, 1987.

The staples 202 are located in pockets formed in a staple cartridge 112 on the jaw 200, with the legs of the staples directed toward the stationary jaw 204. Behind the staple cartridge 112 is a staple pusher 210. The staple pusher has fingers 212 which are directed toward the crowns of respective staples in the staple cartridge. Behind the staple pusher 210 is a driver piston 214. The driver piston is located inside a clamping piston 220, and is pneumatically sealed therein by two circumferential O-rings 216 and 218. The clamping piston 220 is located inside a piston housing 230. The clamping piston 220 is pneumatically sealed inside the piston housing by two circumferential O-rings 222 and 224. Between the later two O-rings are ports 226 and 228 which pass through the clamping piston. These ports are symmetrically located so that the clamping piston can be inserted into the piston housing with either end at the bottom.

Located at the rear of the piston housing is a passageway 232. This passageway is connected to a right angle connector 150 by a pneumatic tubing segment 34. Toward the front of the piston housing is a second passageway 236. This passageway is connected to union 150 by tubing segment 36.

To the lower left of the stapler head 110 is the shaft portion 108 of the stapler. The shaft 108 includes two sections 30 and 32 of pneumatic tubing. The tubing in the shaft portion is connected to quick disconnect fittings of the two inlet ports of the right angle connector 150 (one of which is shown at 54) by quick disconnect fittings, one of which is shown at 106. At the rear terminus of the shaft 108, which is to be connected to the handle 10, is a parallel pneumatic connector 120. Pneumatic connector 120 is removably connected to the handle by pneumatic snap fittings, one of which is shown at 43. The pneumatic tubing 30, 32 is connected to two outlet ports 206 of the connector 120.

When tissue to be stapled is located between the jaws 200 and 204 and it is desired to clamp the tissue between the jaws, the slide 72 is depressed and pressurized gas flows from the handle and into the connector 120. The pressurized gas is carried through tubing section 30 in the shaft portion 108 and through a passageway of the right angle union 150. The pressurized gas passes through tubing segment 34 and passageway 232 to the rear of the clamping piston 220. There the gas is forced into the interface 240 between the clamping piston and the piston housing, where it expands and pushes the clamping piston forward toward the stationary jaw. As the clamping piston moves, it carries the driver piston, staple pusher, and staple cartridge with it. This will clamp the tissue between the staple cartridge and the stationary jaw 204. The clamping piston 220 is now in a position in the housing 230 such that the front passageway 236 opposes port 228 of the clamping piston.

With the tissue securely clamped between the jaws, the user moves and rotates the trigger safety and pulls the trigger to implant the staples. Pressurized gas flows through connector 120, pneumatic tubing 32, the connector 150, and tubing segment 36 to passageway 236. The pressurized gas then flows through port 228 in the clamping piston and into space 242 at the rear of the driver piston. The expanding gas in this space pushes the driver piston 214 forward against the rear of the staple pusher 210, whereby uniform pressure is applied to the pusher and its fingers. The fingers then drive the staples out of the pockets of the staple cartridge, through the tissue, and against the anvil or into the receivers of the stationary jaw. When the trigger is released, the pressurized gas to the driver piston and clamping piston is vented through the handle, releasing the jaw 200 from the stapled tissue.

The arrangement of FIG. 2 is more fully described in concurrently filed United States patent application serial number (ETH-741), entitled "PNEUMATICALLY ACTUATE SURGICAL STAPLER HEAD."

The pressurized gas developed in the handle portion 10 is conducted to the clamping and stapling mechanisms in the stapler head 110 through pneumatic tubing 30 and 32 and joints 20 and 22 which connect the handle portion of the stapler to the stapler head through an interchangeable shaft portion 108, as shown in FIGS. 1 and 2. The shaft portion is connected to the handle portion and the stapler head by quick disconnect, snap-lock fittings similar to those found on many pneumatic instruments, and by the rotating connectors 120 and 150. The rotating two-passage connectors allow the stapler head and shaft portion to be rotated with respect to the handle portion while maintaining the integrity of the pressurized gas lines.

The parallel connector 120 at the joint 20 of the handle and shaft is shown in perspective in FIG. 3a, and in cross-section in FIG. 3b. The parallel connector 120 of FIG. 3b includes a molded half 122 having inlet ports 124 and 126. Attached to the inlet ports are female quick disconnect fittings 43 and 46. Port 124 leads to a passageway 127 in the center of the connector, and port 126 leads to a passageway 129 offset from the center of the connector. Passageway 129 intersects a circular passageway 130 located in a plane normal to the plane of FIG. 3b. A cross-sectional view taken through opposite sides of circular passageway 130 is shown in FIG. 3b.

The parallel connector 120 includes a second molded half 132 having outlet ports 134 and 136, which connect with passageways 127 and 131. Attached to these outlet ports are male quick disconnect fittings 34 and 36. The two halves 122 and 132 are held together by a compression fitting 140. At the interface of the two halves are two O-rings 142 and 144, shown in cross section. The compression fitting is tight enough to maintain the integrity of the O-ring sealed pneumatic passageways, but is sufficiently loose across the interface to permit the two halves to be rotated with respect to each other. The smaller O-ring 142 seals the center passageway 127 inside the O-ring and separates the center passageway from the outer circular passageway 130. The larger O-ring 144 seals the outer perimeter of the circular passageway 130.

As the two halves of the parallel connector are rotated with rotation of portions of the stapler, the molded connector halves rotate about the center passageway 127 which connects inlet port 124 to outlet port 134. While passageways 131 and 129 are shown in alignment in FIG. 3b, this alignment will no longer occur as the halves of the connector are rotated. Instead, the passageways 131 and 129 will rotate about the center of the connector in the arc of circular passageway 130 to which they connect. Thus, the pneumatic path from inlet port 126 to outlet port 136 will comprise passageway 129, the arcuate sections of circular passageway 130, and passageway 131. The connector thereby allows relative rotation of portions of the stapler while maintaining the separation and integrity of the pneumatic lines.

The female quick disconnect fittings 43 and 46 are each seen to have a flared outer end 44 and 47, which engage mating male fittings. The attached ends of the fittings 43 and 46 are narrowed in diameter as shown at 45 and 49 to sealingly engage the mating fittings. The male fittings 34 and 36 are of the same configuration, with their flared ends 33 and 38 attached to respective ports 134 and 136. The narrowed diameter portions of the male fittings engage sealing O-rings 35 and 37. When male and female fittings are engaged, pneumatic sealing is provided by the compression of the O-rings 35 and 37 within the narrowed diameter portions 45 and 49 of the female fittings. The fittings thus maintain a secure pneumatic seal while being easily connected and disconnected as various parts of the stapler system are interchanged. The fittings are suitable for engagement with each other as shown at 54 and 106 of FIG. 2, and may also be connected directly to tubing segments as shown at 206 in FIG. 2 when disconnection is not required.

A right angle connector 150, such as that employed at the joint 22 of the shaft portion and stapler head in FIG. 2, is shown in perspective in FIG. 4a, and in cross-section in FIGS. 4b and 4c. Like the parallel connector 120, the right angle connector 150 includes inlet ports 152 and 154 containing quick disconnect fittings 52 and 54, and outlet ports 162 and 164 which contain quick disconnect fittings 62 and 64. A central passageway 156 connects inlet port 152 to outlet port 162, and a circular passageway 158 connects inlet port 154 to outlet port 164 by way of passageways 166 and 168. The same rotational concept applies, whereby passageways 166 and 168 rotate around the central passageway 156 in the arc of circular passageway 158.

What is claimed is:
1. In combination:
a surgical stapler having two pneumatic lines connecting a triggering mechanism and a driving mechanism by means of a shaft, said pneumatic lines traversing said shaft, said pneumatic lines attached to a pneumatic connector comprising:
two mating parts, each said mating part containing two portions of pneumatic lines, one mating part rotatable relative to the second mating part about an axis coincident with both mating parts; and
each said pneumatic line portion of one part corresponding to a pneumatic line portion of the second mating part such that when said mating parts of said connector are mated fluid paths are established through completed pneumatic lines independent of the rotational orientation of one mating part with respect to the other mating part.

2. The combination of claim 1 wherein said driving mechanism is separable from and rotatable at right angles to said shaft, the pneumatic lines in said driving mechanism and said shaft connected by means of a second pneumatic connector comprising:
two mating parts, each said mating part containing a plurality of pneumatic line portions, one mating part rotatable relative to the second mating part about an axis coincident with both mating parts;
each said pneumatic line portion of one part corresponding to a pneumatic line portion of the second mating part such that when said mating parts of said connector are mated fluid can flow through each completed pneumatic line independent of the rotational orientation of one mating part with respect to the other mating part.

3. The combination of claim 1, wherein upon the mating of both parts fluid can flow through each completed pneumatic line by means of a mating passageway contained at the interface of said parts;
wherein one of said mating passageways comprises an annular opening concentric with the coincident axis of said mating parts such that a pneumatic line portion of one mating part is connected to said mating passageway and the corresponding pneumatic line portion of the second mating part is connected to said mating passageway.

4. The combination of claim 3 wherein said driving mechanism is separable from and rotatable at right angles to said shaft, the pneumatic lines in said driving mechanism and said shaft connected by means of a second pneumatic connector comprising:
two mating parts, each said mating part containing a plurality of pneumatic line portions, one mating part rotatable relative to the second mating part about an axis coincident with both mating parts;
each said pneumatic line portion in one part corresponding to a pneumatic line portion in the mating part such that on the mating of both parts fluid can flow: through each completed pneumatic line by means of a mating passageway contained at the interface of said parts;
wherein one of said mating passageways comprises an annular opening concentric with the coincident axis of said mating parts such that a pneumatic line portion of one mating is connected to a pneumatic line portion of the other mating part by way of said annular opening.

5. The combination of claim 1, wherein upon the mating of both parts fluid can flow through completed pneumatic lines by means of mating passageways at the interface of said parts, one of said mating passageways comprising an annular opening concentric with the coincident axis of said mating parts.

6. The combination of claim 5 wherein said driving mechanism is separable from and rotatable at right angles to said shaft, said driving mechanism being connected to said pneumatic lines in said shaft by means of a second pneumatic connector comprising:
two mating parts, each said mating part containing a plurality of pneumatic line portions, one mating part rotatable relative to the second mating part about an axis coincident with both mating parts;

each said pneumatic line portion in one part corresponding to a pneumatic line portion in the mating part such that on the mating of both parts fluid can flow through completed pneumatic lines by means of a mating passageway contained at the interface of said mating parts, wherein one of said mating passageways comprises an annular opening concentric with the rotation axis of said mating parts.

7. The pneumatic connector of claim 1 wherein each of the completed pneumatic lines is sealed from the environment to provide continuous fluid flow through the connector.

8. The connector of claim 7 wherein said pneumatic line portions are generally parallel to the axis of the mating parts of the connector.

9. The connector of claim 7 wherein said pneumatic line portions of one part are generally at right angles to said pneumatic line portions of the other part.

10. The connector of claim 1 wherein one completed line is coincident with said coincident axis and a portion of said second completed line passes radially about said coincident axis.

11. The pneumatic connector of claim 1 wherein, upon the mating of both parts, fluid can flow through a completed pneumatic line by means of a mating passageway at the interface of said parts;

said mating passageway comprising an annular opening concentric with the rotation axis of said mating parts such that a pneumatic line portion of one mating part is in fluidic connection with a corresponding pneumatic line portion by means of said mating passageway.

12. The pneumatic connector of claim 11 wherein each of the completed pneumatic lines is sealed from the environment to provide continuous fluid flow through the connector.

13. The connector of claim 12 wherein those portions of the fluid path established by the pneumatic line portions are generally parallel to said coincident axis.

14. The connector of claim 13 wherein fluid enters the connector through one of said mating parts at generally right angles to said coincident axis of the other mating part.

15. The connector of claim 11 wherein two completed fluid lines are formed by the mated parts such that one completed line passes along said coincident axis and the second completed line passes radially about said coincident axis such that upon mating, said second completed pneumatic line including a radial passageway at the interface of said parts, said passageway sealed within said mated parts from said one completed line.

* * * * *